United States Patent [19]

Rosenbaum

[11] Patent Number: 4,564,518

[45] Date of Patent: Jan. 14, 1986

[54] OPHTHAMOLOGICAL METHOD FOR TESTING TEAR FLOW AND COMPOSITION FOR USE IN SAME

[76] Inventor: Joseph G. Rosenbaum, 23511 Chagrin Blvd., Beachwood, Ohio 44122

[21] Appl. No.: 603,929

[22] Filed: Apr. 26, 1984

[51] Int. Cl.$^4$ ............................................. A61K 49/00
[52] U.S. Cl. .......................................... 424/9; 424/7.1
[58] Field of Search ..................................... 424/9, 7.1

[56] References Cited

U.S. PATENT DOCUMENTS 3,306,820 2/1967 Krezanoski .............................. 424/9
4,341,223 7/1982 Lutz ........................................ 424/9
4,350,676 9/1982 Laties ...................................... 424/9

Primary Examiner—Sam Rosen
Attorney, Agent, or Firm—Isler and Ornstein

[57] ABSTRACT

A process and composition for ophthamological testing for patency in which there is direct observation of the rate and direction of flow of the composition toward and into the punctal orifices. The composition is a suspension of highly visible, minute particles in an isotonic liquid carrier, a drop of which is applied to the eyeball and the movement of the discrete particles observed under magnification at the meniscus formed at the margin of the eyelids.

13 Claims, No Drawings

OPHTHAMOLOGICAL METHOD FOR TESTING TEAR FLOW AND COMPOSITION FOR USE IN SAME

BACKGROUND OF THE INVENTION

In the field of ophthamology, there are certain symptoms, such as a burning sensation, dryness or excessive wetness around the area of the eye, which may indicate obstruction of the channels which normally serve to drain or discharge moisture from the surface of the eyeball.

The moisture for the eyeball is produced by the tear glands, mostly above and behind the upper eyelids. The tear flow down across the eyes and the moisture collects at the margins of the eyelids. From there the accumulation of fluid flows toward the corner of the eye, adjacent the nose, where the upper punctum and the lower punctum each provide a drain orifice which leads to a sac common to both punctae. The sac has a discharge opening leading into the naso-lacrimal duct, which, in turn, discharges the drained moisture into the nose passages, where it normally evaporates. The combination of punctum, sac and duct comprise the normal outflow channel for the moisture normally supplied to the eyeball by the tear ducts. The patency or openness of this channel determines the efficacy of the moisture drainage from the eye.

When the channel becomes partially or wholly obstructed for any reason, discomfort may occur and result in certain symptoms, such as aforementioned, which make it desirable to test the patency of the tear outflow channel to determine if, in fact, it is not providing adequate moisture outflow.

The method that currently is most favored for testing patency is the "Jones test" which utilizes a fluorescein dye. A drop of the dye is applied to the eyeball and the change in concentration of the dye on the eyeball is visually observed over a time span which may range up to fifteen minutes, depending on the patency of the outflow channel and the quantity of moisture produced by the tear ducts. Ordinarily, the observation time is 5-10 minutes. If there is adequate patency, there is a visually determinable change in the observed concentration of the dye over a relatively short time span. If obstruction exists, the change in concentration occurs, if at all, much more slowly. Understandably, it takes considerable skill and experience for the observer to correctly interpret the observed changes in the concentration of the dye.

Alternatively, the nostril of the nose is packed with tissue or other soft, absorbent material before the dye is applied to the eyeball. Then, after a given period of time, e.g. seven minutes, the packing is removed and exposed to a cobalt blue light to determine the absence or presence of the fluorescein dye and attempt to determine about how much has traveled from the eye into the nose, as a measure of patency.

If it is concluded, as a result of the foregoing procedure, that an obstruction exists in the outflow channel, then more accurate and sophisticated procedures, such as radio-active injection of the punctum, are available for establishing the specific location and character of the obstruction.

Regardless of which variation or combination of the fluoroscein dye test is utilized, it is time-consuming, and its interpretation can be as wide-ranging and indeterminate as the subjectiveness and experience of the observer warrants.

SUMMARY OF THE INVENTION

In view of the foregoing, the present invention is directed to overcoming the disadvantages experienced with prior art ophthamological patency tests.

It is a primary object of my invention to provide a patency test which relies upon direct observation of the moisture flow from the eyeball to the punctum.

Another object of my invention is to provide a method or procedure for a patency test which utilizes suspended solids as visual tracer elements for the observation of moisture flow to the punctum.

A further object of my invention is to provide a composition for use in my improved patency test procedure.

Still another object of my invention is to provide an efficient and effective patency test which can be performed and concluded in far less time then is currently required for the prior art patency tests.

To accomplish the foregoing, I utilize minute particles of material suspended in a suitable liquid carrier. This composition is applied to the eyeball. The flow of the particles on and from the eyeball is visually observed through a slit-lamp microscope, by means of which the rate and direction of moisture drain from the eyeball can be instantaneously observed to determine patency or the lack thereof.

Other objects and advantages of my invention will become apparent during the course of the following description, which will be readily understandable to those skilled in the art, without the need for reference to any drawings or the like.

DESCRIPTION OF THE PREFERRED EMBODIMENTS

The compositions which are preferred for use in the improved patency test, may broadly be described as natural or synthetic nacreous pigments in the form of a paste or suspension. The discrete particles are non-toxic and are of crystalline, platelet form and are highly reflective, such as for example in natural pearl essence.

In performing my improved patency test, such a composition, consisting essentially of a suspension of minute discrete particles in a liquid carrier, is utilized. A drop or so of the liquid suspension is applied to the eyeball. The natural flow of liquid on the eyeball, as determined by the wiping effect of the eyelids on the eyeball, creates a liquid meniscus at the margins of the eyelids, where the eyeball is exposed. The meniscus forms a pathway for the flow of liquid toward the corner of the eye, adjacent to the nose.

As previously disclosed, the liquid drains from the corner of the eye into the punctal orifices provided by the upper punctum and lower punctum of each eye. The dual punctae drain into the nose, through the outflow channels previously described, where the moisture normally evaporates. In this manner, the moisture normally supplied to the eye by the tear glands, drains from the eye.

After a drop of the patency test composition has been applied to the eyeball, the flow of the suspended particles in the meniscus and near the corner of the eye is immediately observed, preferably under a magnification of at least 10X with the aid of a biomicroscope or slit-lamp magnifier. The discrete solid particles, which are substantially insoluble or not highly soluble in the liquid carrier or in the natural effluent of the tear glands can readily be observed flowing toward the corner of the eye in the pathway or conduit created by the meniscus at each eyelid, if the outflow passage is not obstructed. If there is any impediment to the outflow, either in the punctal orifice or elsewhere in the outflow passage, the particles move more slowly or sluggishly or perhaps not at all, in the direction of the corner. The punctal orifices in the corner of the eye can also be observed to determine if the particles are flowing past one punctum and into the other, thus indicating blockage. This condition of obstructed flow of the particles is also readily and instantaneously observable. If the test indicates an impediment to normal outflow from the eye, necessary measure to correct the situation or more sophisticated and precise tests are undertaken.

This patency test can be completed within a very short time frame of a minute or so, thus effecting a considerable time saving for the ophthamologist over the prior art procedures.

It will also be noted that instead of indirectly attempting to determine patency by such means as a change or dilution of dye concentration, as in the prior art, the herein disclosed test is based upon a direct observation of the rate and direction of flow of ocular liquid from the eyeball to and into the point of normal drainage. Thus, this test has the advantage of accuracy and speed, with no need for reliance upon interpretation of indirect observations.

The composition which is utilized in my patency test must, above all, not be harmful or injurious to the eye. To this end, I prefer to use a liquid carrier which is predominantly water and which is isotonic i.e. comparable to the artificial tears solution which are commonly available. These solutions attempt to simulate the composition of the natural moisture of the eye. They are sterile solutions consisting principally of water and usually containing small amounts of additives to improve lubricosity and viscosity and provide preservatives. Examples of such additives are polyvinyl alcohol, cholorobutanol, benzalkonium chloride and sodium chloride. Such artificial tears are sold under a wide variety of trademarks, two of which are Hypo Tears by CooperVision Pharmaceuticals, Inc. and Liquifilm Tears by Allergan America.

The preferred solid particles are a crystalline, highly light-reflective, nacreous pigment material whose largest particle dimension is not greater than 100 microns and preferably in the range of 10–40 microns, for ready flow and discharge through the normal outflow passages.

The specific gravity of the particles must be of such value relatively to the specific gravity of the liquid carrier, that the particles will be suspended in and travel with the flow of the carrier on the eyeball and, particularly, in the previously described meniscus. For example, if the liquid carrier has a specific gravity of 1.00, then the solid particles could have a specific gravity of about 1.75, but not exceeding three times the specific gravity of the liquid carrier, depending on the viscosity of the mix.

For purposes of clearly observing the discrete particles, sparkling particles having a high light-reflectivity characteristic are preferred, particularly when a light beam is directed onto them through a slit-lamp.

Additionally, high visibility of the particles can also be attained by using colored particles whose flow progress will be readily apparent under strong light and magnification.

Examples of preferred nacreous pigment materials are natural pearl essence and lamellar titanium dioxide-coated mica. Although there are other inorganic nacreous pigments, such as basic lead carbonate and lead hydrogen phosphate, these particles have a higher specific gravity than is ordinarily desirable for the test composition.

Having thus described my invention, I claim:

1. A method for ophthamological patency testing, comprising the steps of
   (a) applying a substantially isotonic liquid suspension of minute light reflective solid particles to the eye,
   (b) permitting said suspension to form a meniscus at the margin of the eyelids, and
   (c) observing the rate of flow of said particles in said meniscus toward the punctal orifices.

2. A method as defined in claim 1, wherein said step of observing said particles is performed with a magnification of at least 10X of said particles.

3. A method as defined in claim 1 or 2, wherein said particles have a high light-reflectivity, and including the step of directing a light beam onto said particles while observing them.

4. A method as defined in claim 1 or 2, wherein said particles are in the form of non-toxic nacreous pigments.

5. A composition for application to the eye in an ophthamological patency test, comprising a substantially isotonic liquid carrier which is substantially non-irritating to the eye, and a quantity of highly visible, minute, discrete, light reflective particles in said liquid carrier, said particles having a specific gravity of a value in relation to the specific gravity and viscosity of the liquid carrier, which will permit said particles to be suspended in and travel with the flow of said liquid carrier.

6. A composition as defined in claim 5, wherein the major ingredient of said liquid carrier is water.

7. A composition as defined in claim 5, wherein said liquid carrier is comparable in composition to artificial tears.

8. A composition as defined in claim 5, wherein said particles are selected from the group consisting of natural nacreous pigments and inorganic nacreous pigments.

9. A composition as defined in claim 5, wherein said particles are lamellar, crystalline and have high light-reflectivity.

10. A composition as defined in claim 5, wherein said particles have a color transmitting characteristic sufficient to permit visual identification of discrete particles in said suspension.

11. A composition as defined in claim 5, wherein said particles are selected from the group consisting of natural pearl essence and titanium dioxide-coated mica.

12. A composition as defined in claim 5, 6, 7, 8, 9, 10 or 11, wherein said discrete particles do not exceed 100 microns in any one dimension.

13. A combination as defined in claim 5, 6, 7, 8, 9, 10 or 11, wherein said discrete particles have a specific gravity value of not more than three times the specific gravity of the liquid carrier.

* * * * *